(12) United States Patent
Kwant et al.

(10) Patent No.: US 6,242,006 B1
(45) Date of Patent: *Jun. 5, 2001

(54) β-LACTAM GRANULES FREE OF ORGANIC SOLVENTS

(75) Inventors: Gerard Jan Kwant, Nootdorp; Nicolaas Henricus Scheffers, Rozenburg, both of (NL)

(73) Assignee: Gist-Brocades B.V. (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,245
(22) PCT Filed: Jul. 15, 1997
(86) PCT No.: PCT/EP97/03877
  § 371 Date: Dec. 24, 1998
  § 102(e) Date: Dec. 24, 1998
(87) PCT Pub. No.: WO98/02145
  PCT Pub. Date: Jan. 22, 1998

(30) Foreign Application Priority Data

Jul. 16, 1996 (EP) .................................................. 96202003

(51) Int. Cl.$^7$ ....................................................... A61K 9/14
(52) U.S. Cl. ............................. 424/489; 424/464; 424/451
(58) Field of Search ..................................... 424/489, 464, 424/451

(56) References Cited

U.S. PATENT DOCUMENTS

| | | | |
|---|---|---|---|
| 4,950,484 | * | 8/1990 | Olthoff et al. ........................ 424/464 |
| 5,948,422 | * | 9/1999 | Van Koutrik et al. ................ 424/408 |

FOREIGN PATENT DOCUMENTS

| | | | |
|---|---|---|---|
| 0281200 | | 9/1988 | (EP) . |
| 0330284 | * | 8/1989 | (EP) ................................ A61K/9/16 |
| 2186230 | | 1/1974 | (FR) . |
| WO24337 | | 8/1996 | (WO) . |

* cited by examiner

*Primary Examiner*—Thurman K. Page
*Assistant Examiner*—Isis Ghali
(74) *Attorney, Agent, or Firm*—Bierman, Muserlian and Lucas

(57) ABSTRACT

β-Lactam granules free of organic solvents have been provided for. Also a process to prepare the same by applying during the granulation only water as binding solvent has been disclosed.

3 Claims, No Drawings

β-LACTAM GRANULES FREE OF ORGANIC SOLVENTS

This application is a 371 of PCT/EP97/03877 filed Jul. 15, 1997.

The present invention relates to β-lactam granules free of organic solvents and a process to prepare the same.

TECHNOLOGICAL BACKGROUND AND FIELD OF INVENTION

For the manufacturing of tablets and capsules containing oral grade penicillins or cephalosporins it is generally found that the crystalline material has no satisfactory flowability so that controlled dosage during tablet and capsule manufacturing-processes is not guaranteed. Therefore it is customary to produce a granulate first by mixing the crystalline powder (1–30 μm) with a small amount of organic solvent (e.g. alcohol) sometimes diluted with water. It is required then to admix other components as binders (e.g. PVP) and fillers (e.g. lactose) for obtainment of granulates with satisfactory particle size distribution and strength. However, it will not be possible to achieve a high dosage per tablet unless relatively large tablets are made.

The granulation process generally takes place in a high shear mixer granulator by which dense particles of a suitable particle size distribution are produced. After the granulation process the material (particles of approximately 400–500 μm average diameter) is dried. It is found that while using only water as binding liquid (i.e. no alcohol, no binding agents) wherein Pen VK has been solved which liquid leads to binding into granules during the drying process, the batch-wise operated high shear granulators can not give a satisfactory particle size distribution while excessive fouling of the apparatus occurs.

The use of an organic solvent in this process is a clear disadvantage because of the fact that one has to dry the final product extensively due to the required low levels of solvent in the final dosage form. From a process point of view one would have remarkably less environmental problems if the organic solvent could be circumvented.

Furthermore, the absence of binders could give granulates which can be used in high potency tablets or capsules.

We have found now two granulation methods wherein the organic solvent is not needed for obtaining water soluble penicillins, for instance Pen VK granules. The granulation of Pen VK is carried out using only water as binding solvent while no other additives (like binder materials) are required resulting in β-lactam granules essentially free of organic solvent, viz. with no more organic solvents than the β-lactams contain before the formation of granules.

SUMMARY OF THE INVENTION

The present invention provides β-lactam granules being free of organic solvents, especially granules of the potassium salts of β-lactams, preferably granules of the potassium salt of penicillin V. Also a process to prepare said β-lactam granules has been provided for, viz. by applying during the granulation essentially only water as binding solvent. Preferably said process is carried out in a batch-wise operated fluidized bed granulator, more preferably by applying top spray of water. Alternatively said process is carried out in a continuous mixer. Finally, also tablets or capsules comprising said granules do form an aspect of this invention.

DETAILED DESCRIPTION OF THE INVENTION

The two granulation methods, wherein the use of organic solvents have been avoided, consist essentially of the application of a batch-wise operated fluidized bed granulator or a continuous high-shear mixer in combination with a fluidized bed dryer. The application of these two granulation methods results in granules of β-lactams, for instance the potassium salt of penicillin V with a satisfactory particle size distribution, viz. mainly between 100 and 1400 μm, bulk and tapped density and particle strength.

The first method comprises the following steps:

A certain amount of crystalline β-lactam powder, for instance from the potassium salt of penicillin V, is added to a fluidized bed granulator wherein air, conditioned to a certain temperature and humidity, is passed as to move the solids vigorously. After adjustment of the temperature of the bed to the inlet air temperature (typically 0–60° C.), water is added by using spray nozzles (top-spray). Preferably so called two-phase nozzles using compressed air are applied. Within approximately 30–60 minutes 5 to 200%, preferably 10–100 wt % of water is added to the bed mass during which the bed temperature drops, typically to 20–30° C. The exact amount and temperature depend on the air humidity, air flow rate and air temperature. The amount of water can in principle be much larger but this may cause unpracticle long operating times. After reaching a satisfactory particle size (distribution) the water dosage is stopped and the bed mass is dried until the bed temperature reaches a predetermined value (e.g. 50–60° C.).

The bed is emptied while the granulate is passed over a grinder-sieve in which the large (off-spec) particles are broken to a suitable size, viz. between 25 and 2000 μm, preferably between 100 and 1400 μm. The process can be carried out in fluid beds of different sizes.

According to the second method, the crystalline material is added on the front end by an adjusted flow rate (e.g. using a screw device) to a continuous high shear mixer granulator such as the Lödige CB type of machine. This consists of a horizontal axis provided with certain types of paddles, rotating at 1000–3000 rpm. Water is admixed (approximately 5–20 wt %, preferably 10–13 wt %) and after only a few seconds (1–30 s) the wet granulate leaves the machine at the rear end. It is subsequently transferred to a continuous type of dryer such as a continuous fluidized bed dryer. After passing this apparatus (typical residence time 1 hr) the material is milled and sieved and ready for use, preferably in a continuous mode. Several batches of the material can be mixed as to achieve one single batch and subsequently filled in a suitable package (e.g. boxes).

The following examples only illustrate the present invention.

EXAMPLE 1

In a GPCG 1 (Glatt Powder Coater and Granulator, Glatt GmbH) 1 kg of oral grade Pen VK (Gist-brocades) is heated to the inlet temperature of the air (50° C.) while fluidization is commenced (superficial air velocity 8 cm/s). After 6 minutes the water dosage is started (30 g/min, 1.5 bar in nozzle) and the bed temperature dropped to 26° C. After 35 minutes the drying started (air inlet temperature 70° C.) and ended after 44 minutes. Product bulk density 0.5 g/ml, tapped density 0.58 g/ml. Particle size distribution: 200 g >1400 μm, 0.6 g<100 μm, 100 μm<677 g<1400 μm.

EXAMPLE 2

In a GPCG 15 (Glatt GmbH) 10 kg of oral grade Pen VK (gist-brocades) is heated to the inlet temperature of the air (55° C.) while fluidization is commenced. After 40 minutes the granulate was dried and 10.7 kg of water was added; the process ended after 59 minutes. Product bulk density 0.47 g/ml, tapped density 0.55 g/ml. Particle size distribution: 425 g>1400 μm, 185 g<100 μm, 100 μm<8111 g<1400 μm.

EXAMPLE 3

To a Lödige CB 20 (1500 rpm) 116 kg/h or oral grade Pen VK (Gist-brocades) was added continuously and admixed with water (11 wt %). The material was directly transferred to a continuous fluidized bed dryer (Heinen) operating at 70° C. The material passed the dryer and samples were taken after approximately 1.5 h. Product bulk density 0.52 g/ml, tapped density 0.57 g/ml. Particle size distribution: 15% >1400 μm, 11%<100 μm, 100 μm<74%<1400 μm.

What is claimed is:

1. A process to prepare granules of penicillin VK compounds free of organic solvents and additives consisting essentially of:
    adding a crystalline β-lactam powder batch wise to a fluidized bed;
    fluidizing said powder;
    adding water as a binding agent to said powder during fluidization to produce granulates; and
    drying the granules obtained to form penicillin VK having particle size between 25 and 2000 μm.
2. The process of claim 1 wherein the amount of water is 5–200% of the weight of the crystalline pennicillin VK powder.
3. Tablets or capsules produced from the granules prepared by the process of claim 1.

* * * * *